(12) United States Patent
Yanagawa et al.

(10) Patent No.: US 8,575,281 B2
(45) Date of Patent: *Nov. 5, 2013

(54) SULFONIC ACID GROUP-CONTAINING CARBONACEOUS MATERIAL

(75) Inventors: Shinichirou Yanagawa, Kanagawa (JP); Hidesato Kondo, Kanagawa (JP); Michikazu Hara, Kanagawa (JP)

(73) Assignees: Nippon Oil Company, Tokyo (JP); Tokyo Institute of Technology, Tokyo (JP)

(*) Notice: Subject to any disclaimer, the term of this patent is extended or adjusted under 35 U.S.C. 154(b) by 788 days.

This patent is subject to a terminal disclaimer.

(21) Appl. No.: 12/528,051

(22) PCT Filed: Feb. 20, 2008

(86) PCT No.: PCT/JP2008/053346
§ 371 (c)(1),
(2), (4) Date: Oct. 22, 2009

(87) PCT Pub. No.: WO2008/102913
PCT Pub. Date: Aug. 28, 2008

(65) Prior Publication Data
US 2010/0048835 A1    Feb. 25, 2010

(30) Foreign Application Priority Data
Feb. 21, 2007 (JP) ................. 2007-040895

(51) Int. Cl.
*C08G 8/32* (2006.01)

(52) U.S. Cl.
USPC ........... 525/505; 568/579; 568/700; 568/303; 568/716

(58) Field of Classification Search
None
See application file for complete search history.

(56) References Cited

U.S. PATENT DOCUMENTS

| | | | | |
|---|---|---|---|---|
| 3,884,754 A | * | 5/1975 | Kimura et al. | 428/398 |
| 6,025,534 A | * | 2/2000 | Valente et al. | 585/529 |
| 8,013,130 B2 | * | 9/2011 | Yanagawa et al. | 530/500 |
| 2003/0108785 A1 | * | 6/2003 | Wu et al. | 429/44 |
| 2008/0227996 A1 | | 9/2008 | Hara et al. | |

FOREIGN PATENT DOCUMENTS

| | | |
|---|---|---|
| JP | 03-167712 A | 7/1991 |
| JP | 5-43348 | 2/1993 |
| JP | 2002-104816 A | 4/2002 |
| JP | 2004-238311 A | 8/2004 |
| JP | 2006-257234 A | 9/2006 |
| WO | WO-2005/029508 A1 | 3/2005 |

OTHER PUBLICATIONS

Benak et al, (Sulfonation of pyropolymeric fibers derived from phenol-formaldehyde resins) Mar. 2002, 2323-2332.*
Benak et al., Carbon, vol. 40, pp. 2323-2332 (2002).
Shokubai., vol. 18, No. 6, p. 180-184 (1976).
Sekiyu Gakkaishi, vol. 34, No. 3, pp. 201-209 (1991).
Takagaki et al., "Synthesis condition and catalysis of carbon-based solid acid catalysts", 85th Annual Meeting (Spring) of the Chemical Society of Japan, 2B5-43 (2005).
Toda et al., Nature, vol. 438, No. 10, p. 178 (2005).
Takagaki et al., Petrotech, vol. 29, No. 6, pp. 411-416 (2006).
Enda et al., "Carbonization and Activation Behaviors of Waste Phenol Resin", Proceedings of the 16th Annual Conference of the Japan Society of Waste Management Experts, pp. 758-760, C1-8 (2005).
Saiwaishobo, Shin Sekiyu Kagaku Process, pp. 236-241 (1986).

* cited by examiner

*Primary Examiner* — Randy Gulakowski
*Assistant Examiner* — Jeffrey Washville
(74) *Attorney, Agent, or Firm* — Dickstein Shapiro LLP

(57) ABSTRACT

A sulfonic acid group-containing carbonaceous material that is useful as a solid acid catalyst for various reactions such as hydration of olefins and acidolysis reaction of hydroperoxide and also useful as a proton conductor material having excellent proton conductivity is provided. In addition, an economical and environmentally friendly method for producing methyl ethyl ketone is provided. A sulfonic acid group-containing carbonaceous material having high catalytic activities for various acid catalyst reactions and also having high proton conductivity can be obtained by carbonization and sulfonation of a phenolic resin.

10 Claims, No Drawings

US 8,575,281 B2

SULFONIC ACID GROUP-CONTAINING CARBONACEOUS MATERIAL

TECHNICAL FIELD

The present invention relates to a sulfonic acid group-containing carbonaceous material obtained by carbonization and sulfonation of a phenolic resin, a method for producing the same, a solid acid catalyst comprising the same, methods for producing an olefin hydration product, an ether and an ester using the solid acid catalyst, a method for producing an alcohol and/or a fatty acid, by performing hydrolysis reaction of an organic compound containing an ester bond or ether bond using the solid acid catalyst, acidolysis reaction of an aralkyl hydroperoxide, and a proton conductor material comprising the above sulfonic acid group-containing carbonaceous material. In addition, the present invention relates to a method for producing a ketone by dehydrogenation of the olefin hydration product obtained using the above solid acid catalyst.

BACKGROUND ART

Sulfuric acid is an important catalyst widely used for various chemical reactions. However, sulfuric acid has a number of problems, for example, that sulfuric acid is generally required in large amounts, has a problem of apparatus corrosion and requires steps for separating, collecting from the product after the reaction, step for purifying and reusing the collected sulfuric acid, and requires, steps for neutralizing sulfuric acid remained in the product and removing salt generated thereby, and steps of disposal, waste water treatment and the like, and further, these steps require a lot of energy, and the like.

By using a solid acid catalyst as a substitute for mineral acid catalyst such as sulfuric acid, solid acid catalyst is useful as a catalyst for various chemical reactions since the various steps after the above reactions can be omitted or substantially simplified without apparatus corrosion, and various types of solid acids have been developed. Typical solid acids are inorganic compounds such as silica-alumina, crystalline aluminosilicate (zeolite), and heteropoly acid.

On the other hand, the hydration reaction of olefins is an industrially important reaction for the production of alcohols and ketones, and an acid catalyst is used for the reaction. Isopropyl alcohol or 2-butanol is produced by various methods using hydration of propylene or n-butene (Non-Patent Document 1 and Non-Patent Document 2). In many processes of hydration reaction step, sulfuric acid is used as a catalyst. However, in addition to the above-mentioned problems, sulfuric acid has a problem that it generates many by-products, so that solid acid catalysts are also partially used for the purpose of resolving these problems. In this case, the above-mentioned inorganic solid acid catalysts are not used since their activities are generally lowered in the presence of water, and catalysts comprising phosphoric acid supported on an inorganic carrier and the like are used. However, there is a problem that the phosphoric acid is detached from the carrier during the reaction. In addition, a strong acid type of ion-exchange resin, a polymer having a sulfonic acid group on the skeleton of a cross-linked polystyrene, is also used, but its range of use is limited due to problems such as having low heat resistance and expensiveness of the resin. A fluorine-substituted olefin polymer-based solid super strong acid "NAFION" (a registered trademark of DuPont) having heat resistance or the like has been also developed, but it is too expensive to be used for industrial purposes.

In such a situation, a sulfonic acid group-containing carbonaceous material obtained by carbonization and sulfonation of an organic matter such as an aromatic compound or saccharide at a relatively low temperature has been developed, and the material is recently attracting attentions due to high activities for various chemical reactions as a catalyst, excellent heat resistance, inexpensiveness and the like, and the evaluation thereof is being tried as a catalyst for esterification reaction of a fatty acid, hydrolysis reaction of an ester, alkylation reaction and hydration reaction of an olefin, or the like (Non-Patent Document 3, Non-Patent Document 4, Non-Patent Document 5, Patent Document 1, and Patent Document 2). However, for example, with respect to the hydration reaction of an olefin, only an example in which 2,3-dimethyl-2-butene is hydrated to give 2,3-dimethyl-2-butanol in low yield is reported, and the development of a solid acid catalyst with further higher activity has been desired from the viewpoint of practical use. Incidentally, it is well known that normal butene is hydrated to give 2-butanol, and 2-butanol is dehydrogenated to give methyl ethyl ketone. Methyl ethyl ketone is one of the very important industrial chemicals as solvents for paint, ink, adhesive and the like, and cleaning agents for various purposes. 2-butanol is currently produced by a method using sulfuric acid as a catalyst, a method using a heteropoly acid catalyst, or the like. However, the sulfuric acid method has problems of waste sulfuric acid and apparatus corrosion, while the heteropoly acid method involves advanced technology such as using a supercritical state. Therefore, an inexpensive and effective technology for producing 2-butanol has been desired.

In addition, a method for decomposing cumene hydroperoxide to produce acetone and phenol is an industrially very important chemical process. This reaction progresses under acid catalyst, and dilute sulfuric acid is currently used (Non-Patent Document 7). Sulfuric acid aqueous solution is highly corrosive and has a problem of waste sulfuric acid. In addition, sulfuric acid aqueous solution has problems in which a large amount of energy is required to separate the product from the reaction solution, and the like. Therefore, an alternative solid acid catalyst has been desired.

Furthermore, Patent Document 2 and Patent Document 3 disclose proton (ion) conductor materials comprising a sulfonic acid group-containing carbonaceous material obtained by carbonization and sulfonation of various organic matters and also disclose an application to battery as a solid electrolyte. However, the conductivity of these proton conductor materials is still not sufficient and emergence of a material showing further excellent conductivity is anticipated.

On the other hand, it is known since long time that a specific organic matter is heated at high temperature, whereby a carbonized materials with high specific surface area (so-called, activated carbon) is obtained, and a carbonized materials obtained by using phenolic resin as a raw material is also disclosed (for example, Non-Patent Document 6 and Patent Document 4). The carbonized materials disclosed in these documents are obtained by subjecting a phenolic resin to heat treatment at a very high temperature over 700° C. Even though these carbonized materials are sulfonated, many sulfonic acid groups are not introduced, and high catalytic activities for various chemical reactions and the proton conductivity cannot be provided. In this regard, these carbonized materials are much different from the above-described sulfonated carbonaceous materials.

[Non-Patent Document 1] Shokubai, 18(6), 180 (1976)
[Non-Patent Document 2] Sekiyu Gakkaishi, 34(3), 201 (1991)

[Non-Patent Document 3] Domen et al., "Synthesis conditions and catalysis of carbon-based strong solid acids," 85th Annual Meeting (Spring) of the Chemical Society of Japan (2005), 2B5-43

[Non-Patent Document 4] Hara, M. et al. Nature, 438(10), 178, November (2005)

[Non-Patent Document 5] Hara et al., PETROTECH, 29(6), 411 (2006)

[Non-Patent Document 6] Enda et al., "Carbonization and Activation Behaviors of Waste Phenol Resin," Proceedings of the 16th Annual Conference of the Japan Society of Waste Management Experts (2005), 758, C1-8

[Non-Patent Document 7] Shin Sekiyu Kagaku Process, p 239 (1986), SAIWAISHOBO

[Patent Document 1] Japanese Patent Laid-Open No. 2004-238311

[Patent Document 2] International Patent Publication No. WO2005/029508 A1

[Patent Document 3] Japanese Patent Laid-Open No. Hei 3-167712

[Patent Document 4] Japanese Patent Laid-Open No. Hei 5-43348

DISCLOSURE OF THE INVENTION

Objects of the present invention are to provide a sulfonic acid group-containing carbonaceous material having high activities as a solid acid catalyst for various reactions such as hydration of olefins and having excellent proton conductivity and to provide an effective method for producing a compound obtained by the hydration reaction of olefins or the like using a solid acid catalyst comprising the same. In addition, objects of the present invention are to provide an inexpensive and effective method for producing a ketone and also provide an inexpensive and effective method for producing phenols.

As a result of intensive studies in view of the problems of the prior art described above, the present inventors have found that, a phenolic resin is carbonated and sulfonated, whereby a sulfonic acid group-containing carbonaceous material having high activities for various chemical reactions such as hydration reactions and having the high proton conductivity as a proton conductor material is obtained. The present invention has been thus accomplished.

Specifically, a first aspect of the invention is a sulfonic acid group-containing carbonaceous material obtained by carbonization and sulfonation of a phenolic resin.

A second aspect of the invention is the sulfonic acid group-containing carbonaceous material of the first aspect of the invention, wherein the phenolic resin is a novolac type phenolic resin.

A third aspect of the invention is the sulfonic acid group-containing carbonaceous material of the first aspect of the invention, wherein the phenolic resin is a resol type phenolic resin.

A fourth aspect of the invention is a method for producing the sulfonic acid group-containing carbonaceous material of the first, second, or third aspect of the invention, comprising performing carbonization and sulfonation of the phenolic resin.

A fifth aspect of the invention is the method for producing the sulfonic acid group-containing carbonaceous material of the fourth aspect of the invention, comprising performing carbonization of the phenolic resin at a temperature of from 300 to 600° C. and thereafter performing sulfonation at a temperature of from 40 to 250° C. by concentrated sulfuric acid or fuming sulfuric acid.

A sixth aspect of the invention is the method for producing the sulfonic acid group-containing carbonaceous material of the fifth aspect of the invention, comprising performing sulfonation by fuming sulfuric acid.

A seventh aspect of the invention is a solid acid catalyst comprising the sulfonic acid group-containing carbonaceous material of the first, second, or third aspect of the invention.

An eighth aspect of the invention is a method for producing an olefin hydration product, comprising performing hydration reaction of an olefin in the presence of the solid acid catalyst of the seventh aspect of the invention.

A ninth aspect of the invention is a method for producing ethers, comprising performing etherification reaction of an olefin in the presence of the solid acid catalyst of the seventh aspect of the invention.

A tenth aspect of the invention is a method for producing esters, comprising performing esterification by reacting a carboxylic acid with an alcohol in the presence of the solid acid catalyst of the seventh aspect of the invention.

An eleventh aspect of the invention is a method for producing esters, comprising performing esterification by reacting a carboxylic acid with an olefin in the presence of the solid acid catalyst of the seventh aspect of the invention.

A twelfth aspect of the invention is a method for producing an alcohol and/or a fatty acid, comprising performing hydrolysis reaction of an organic compound containing an ester bond or ether bond in the presence of the solid acid catalyst of the seventh aspect of the invention.

A thirteenth aspect of the invention is a proton conductor material comprising the sulfonic acid group-containing carbonaceous material of the first, second, or third aspect of the invention.

A fourteenth aspect of the invention is a method for producing ketones, comprising performing dehydrogenation reaction of the olefin hydration product obtained by the eighth aspect of the invention.

A fifteenth aspect of the invention is the method for producing ketones of the fourteenth aspect of the invention, wherein the olefin hydration product is 2-butanol, and a ketone obtained by the dehydrogenation reaction is methyl ethyl ketone.

A sixteenth aspect of the invention is a method for producing phenols by acidolysis reaction of an aralkyl hydroperoxide, wherein the acidolysis reaction is performed in the presence of the solid acid catalyst of the seventh aspect of the invention.

A seventeenth aspect of the invention is the method for producing phenols by acidolysis reaction of an aralkyl hydroperoxide of the sixteenth aspect of the invention, wherein the aralkyl hydroperoxide is cumene hydroperoxide, and the phenols is phenol.

The sulfonic acid group-containing carbonaceous material of the invention can be supplied in large amounts for industrial use since the material can be easily and inexpensively produced, and has high activities as a solid acid catalyst for various chemical reactions, in particular, hydration reaction and etherification reaction of olefins, esterification reaction of an alcohol with a carboxylic acid, or esterification reaction of an olefin with a carboxylic acid, hydrolysis reaction of an organic compound containing an ester bond or ether bond, decomposition reaction of an aralkyl hydroperoxide, and the like. In a case where the sulfonic acid group-containing carbonaceous material is used as a catalyst for the above reactions, neutralization and purification steps after the reactions are not required, and the catalyst is easily separated and is reusable, so that the objective substance can be inexpensively and effectively produced without the problem of apparatus corrosion. In addition, the sulfonic acid group-containing carbonaceous material of the invention has high proton conductivity as a proton conductor material and can be used for a battery or the like as an inexpensive and high-performance solid electrolyte. Furthermore, according to the present invention, 2-butanol can be inexpensively and effectively produced, and consequently, methyl ethyl ketone can be inexpensively and effectively produced.

BEST MODE FOR CARRYING OUT THE INVENTION

The present invention will be described in detail hereinbelow.

The sulfonic acid group-containing carbonaceous material of the invention is obtained by carbonization and sulfonation of a phenolic resin as a starting material.

The phenolic resin used as the starting material for producing the sulfonic acid group-containing carbonaceous material of the invention is a collective term of resins obtained by an addition condensation reaction of phenols (phenol, cresol, xylenol, resorcin, and the like) with aldehydes (formaldehyde, acetaldehyde, furfural, and the like) using an acid or base catalyst, and modified resins thereof. The phenolic resin used in the invention may be any one of these resins and also may be a so-called special phenolic resin obtained by reacting phenols with a cyclic hydrocarbon having 2 or more carbon-carbon double bonds in the molecule using a Friedel-Crafts catalyst. In particular, phenol-formaldehyde resin obtained by addition condensation of phenol with formaldehyde is preferred. More specifically, a novolac type phenolic resin obtained by addition condensation of phenol with formaldehyde using an acid catalyst, and a resol type phenolic resin obtained by addition condensation of phenol with formaldehyde using a base catalyst are preferred, and the novolac type phenolic resin is particularly preferred. The novolac type phenolic resin is sometimes supplied as a compound with a curing agent to form a three-dimensional crosslinking and is sometimes supplied in the form without a curing agent, and the phenolic resin used in the invention may be either of these resins. When a curing agent is used, a compound that produces formaldehyde by heating is preferred as a curing agent. Specific examples include hexamethylenetetramine, paraformaldehyde and the like, and hexamethylenetetramine is particularly preferred. On the other hand, since a resol type phenolic resin can produce three-dimensional crosslinking structure by heating by itself without using a curing agent, the resin is generally supplied in the form without a curing agent. The form of these phenolic resins may be liquid form or solid form, and the phenolic resins which contain an organic solvent (varnish). In the case of solid form, proper forms such as particulate, powder, granular, spherical, plate, and pellet forms can be used. The phenolic resins are hardened by heat treatment in the coexistence or non-coexistence of a curing agent, and the phenolic resin used in the invention may be either of the form before or after hardening. When hardening is carried out, hardening by heating may be previously carried out, or hardening and carbonization may be simultaneously carried out. In view of the simplification of the steps, it is preferred that hardening and carbonization be simultaneously carried out.

The phenolic resin used in the invention can be used alone or in admixture of two or more kinds. In addition, other organic matters or inorganic matters can be used together within the range so as not to impair the objects and effects of the invention, and it is preferred that the above-described phenolic resin be the main component (50% or more) in that case.

The phenolic resin is frequently thermally hardened and used for the applications mainly in electrical and electronic components, and the like. However, the phenolic resin cannot be melted and remolded after the hardening, and the disposal of the used resin is a problem. As the starting material of the carbon-based solid acid of the invention, such a phenolic resin after being thermally hardened and used for the various applications may be used, and also a composition with other resins, or inorganic or organic particulate or fibrous filler may be used. It is preferred that the above-described phenolic resin be the main component (50% or more) also in these compositions.

The carbonization of the above-described phenolic resin is preferably performed by heating in an inert gas atmosphere such as nitrogen or argon, whereby an amorphous black solid (carbonized materials) is obtained.

The sulfonation is performed by heating in concentrated sulfuric acid or fuming sulfuric acid, whereby a sulfonic acid group is added to the skeleton of the above carbonized materials. The sulfonation can be performed simultaneously with carbonization or can be performed after the carbonization, and it is preferred that the sulfonation be performed after the carbonization.

The conditions for the carbonization and sulfonation are properly selected depending on the type of the phenolic resin to be used and properties of the intended sulfonated carbonaceous material. Preferred embodiments in a case where the carbonization and sulfonation are performed in the separate steps will be described hereinbelow.

The heating for carbonization is preferably performed in an inert gas atmosphere such as nitrogen or argon, at a temperature of from 300 to 600° C. When the temperature of carbonization is below the lower limit of the above range, a sulfonic acid group-containing carbonaceous material obtained by the sulfonation tends to cause problems such as having poor heat resistance, or much content soluble in water or organic matter. On the other hand, when the temperature is above the upper limit of the above range, a sufficient amount of sulfonic acid groups cannot be provided upon the sulfonation, and the catalytic activities for various chemical reactions of the resulting sulfonic acid group-containing carbonaceous material tend to be insufficient, and also the proton conductivity tends to be insufficient as a proton conductor material.

The heating time period of carbonization is from 1 to 100 hours, and preferably from 2 to 15 hours. When the time period for the carbonization is below the lower limit of the above range, a sulfonic acid group-containing carbonaceous material obtained by the sulfonation tends to cause problems such as having poor heat resistance, or much content soluble in water, organic matter, or the like. On the other hand, the necessary carbonization sufficiently progresses at the upper limit time of the above range, so that it is unnecessary to spend a time above the upper limit time.

A sulfonating agent used for the sulfonation is concentrated sulfuric acid or fuming sulfuric acid. In order to increase a sulfonic acid group content in the sulfonic acid group-containing carbonaceous material to be produced, it is preferable to use fuming sulfuric acid. Thereby, the sulfonic acid group-containing carbonaceous material having high catalytic activities for various reactions is obtained. The amount of concentrated sulfuric acid or fuming sulfuric acid to be used is not particularly limited, and is 5 to 100 times (mass ratio) and preferably 10 to 80 times as the amount of carbonized material to be sulfonated. When the amount is below the lower limit of the above range, sufficient amounts of sulfonic acid groups cannot be provided to the carbonized material, and the catalytic activities for various chemical reactions of the resulting sulfonic acid group-containing carbonaceous material tend to be insufficient, and also the proton conductivity tends to be insufficient as a proton conductor material. On the other hand, when the amount is above the upper limit of the above range, excessive concentrated sulfuric acid or fuming sulfuric acid is used, so that the cost is increased=including the cost for disposal of used sulfuric acid.

The temperature of sulfonation is from 40 to 250° C. and preferably from 80 to 200° C. When the temperature of sulfonation is below the lower limit of the above range, a sufficient amount of sulfonic acid groups cannot be provided to the carbonized material, and the catalytic activities for various chemical reactions of the resulting sulfonic acid group-containing carbonaceous material tend to be insufficient, and also the proton conductivity tends to be insufficient as a proton conductor material. On the other hand, when the temperature of the sulfonation is above the upper limit of the above range, the added sulfonic acid groups tend to decompose. In addition, an operation for the sulfonation procedure becomes difficult.

The time period of sulfonation can be properly selected, and the sulfonation is performed preferably in the range over 2.5 hours and not over 30 hours. When the time period of sulfonation is below the lower limit of the above range, a sufficient amount of sulfonic acid groups cannot be provided to the carbonized material, and the acid content is not saturated. Therefore, the resulting product is inevitably insufficient as the sulfonic acid group-containing carbonaceous material. In addition, the proton conductivity tends to be insufficient as a proton conductor material. On the other hand, necessary sulfonation sufficiently progresses at the upper limit time of the above range, so that it is unnecessary to spend a time above the upper limit time.

After the carbonization and sulfonation steps, excessive sulfuric acid is removed by washing preferably with hot water, and the resulting mixture was further dried, whereby the sulfonated carbonaceous material of the invention can be obtained. The washing with hot water can be easily carried out, for example, under reflux at about 100° C. by means of Soxhlet extraction or the like. Also, the washing time can be shortened by washing at higher temperature under pressure.

In general, the degree of carbonization when an organic matter is carbonized by heating is frequently represented by the degree of graphitization, and the intensity ratio of G-peak which appears near a wavenumber of 1580 $cm^1$ and D-peak which appears near 1400 $cm^{-1}$ in Raman spectroscopy is utilized as one of the indexes showing the degree of graphitization. For example, in the conventional sulfonic acid group-containing carbonaceous material obtained by using aromatic hydrocarbon, heavy oil, petroleum pitch, glucose and the like as starting materials disclosed in Non-Patent Document 5, the degree of graphitization is determined according to Raman spectroscopy, or the size of carbon sheet is estimated using Raman spectroscopy. However, with respect to the sulfonic acid group-containing carbonaceous material of the invention, a clear Raman spectrum is not obtained, and the degree of carbonization cannot be confirmed based on this index. Based on the above, it is considered that the sulfonic acid group-containing carbonaceous material of the invention is different in its structure from the conventional sulfonic acid group-containing carbonaceous material.

The sulfonic acid group-containing carbonaceous material of the invention is substantially amorphous such that any structure cannot be confirmed from an X-ray diffraction pattern.

The acid group content of the sulfonic acid group-containing carbonaceous material of the invention is 1 mmol/g or more and preferably 1.5 mmol/g or more. When the acid group content is below the lower limit of the above range, the catalytic activities for various chemical reactions tend to be insufficient as a solid acid. In addition, the proton conductivity tends to be insufficient as a proton conductor material. Incidentally, the term "the acid group content" used herein refers to the acid group content of the sulfonic acid group-containing carbonaceous material determined by back titration and refers to the content of the acid groups of the combination of sulfonic acid groups produced by the sulfonation and carboxylic acid groups and phenolic hydroxyl groups produced upon the carbonization and/or sulfonation.

The atomic ratio of sulfur to carbon (molar ratio) in the sulfonic acid group-containing carbonaceous material serves as a measure of the content of the sulfonic acid groups added and introduced into the sulfonated carbonaceous material. The atomic ratio of sulfur to carbon (molar ratio) in the sulfonic acid group-containing carbonaceous material of the invention is from $1.5 \times 10^{-2}$ to $8 \times 100^{-2}$, and preferably from $2 \times 10^{-2}$ to $7 \times 10^{-2}$. When the ratio is below the lower limit of the above range, activities for various reactions as a solid acid catalyst tend to be insufficient. On the other hand, it is difficult to obtain an atomic ratio of sulfur to carbon above the upper limit of the above range by the method of the invention.

The sulfonic acid group-containing carbonaceous material of the invention is a powdery shape at the stage of production. Upon being used as a solid acid catalyst for various reactions, the material may be a powdery shape and also may be formed into a granular, spherical, plate, or pellet shape or the like. When the material is formed into these shapes, an inorganic substance called binder may be blended to carry out forming. The binder is blended for the purpose of the improvement of formability, the improvement of mechanical properties such as strength of formed catalyst, rub resistance and the like, and alumina, alumina-boria, silica-alumina and the like are preferably used.

The sulfonic acid group-containing carbonaceous material of the invention has such acid strength and acid content as to be useful for various chemical reactions as a solid acid catalyst. The sulfonic acid group-containing carbonaceous material of the invention functions as a solid acid catalyst even under hydrophobic conditions, and specifically useful as a catalyst, preferably, for reactions under various polar conditions such as hydration reaction and etherification reaction of olefins, esterification reaction of alcohol with carboxylic acid, and hydrolysis reaction of organic compound containing an ester bond or ether bond. Namely, the material is useful as a catalyst for these polar reactions since excellent activity and durability are exhibited in reactions using a polar substance such as alcohol, carboxylic acid or water as a reactive substrate.

Hydration reaction of olefins (reaction of olefins with water), etherification reaction of olefins (reaction of olefins with alcohol), and esterification reaction (reaction of carboxylic acid with alcohol), and hydrolysis reaction of organic compound containing an ester bond or ether bond, wherein the sulfonic acid group-containing carbonaceous material of the invention is used as a solid acid catalyst, will be explained hereinbelow.

The olefins used in the hydration reaction and etherification reaction of olefins in the invention are not particularly limited, and any one of straight, branched and cyclic ones may be used. Olefins having a carbon number of 2 to 5, specifically, propylene, and butenes such as 1-butene, 2-butene and isobutene are preferably used. In addition, the water to be used in the hydration reaction is not particularly limited, and ion-exchanged water or distilled water (including vapor condensate) is preferably used.

The alcohols used for the etherification reaction in the invention are not particularly limited, and alcohols having a carbon number of 1 to 4, specifically, methanol, ethanol, isopropyl alcohol, t-butyl alcohol and the like are preferably used. The molar ratio of water or alcohols to olefins is not particularly limited and generally set to 0.1 to 10, preferably to 0.3 to 7, and further preferably to 1 to 5. When the amount of water or alcohols is too small, a side reaction such as dimerization of olefin occurs, and when it is too large, the productivity is deteriorated.

As the alcohols used for the esterification reaction in the invention, the same alcohols as those described above can be used. Also, the carboxylic acids include saturated or unsaturated carboxylic acids having a carbon number of 1 to 4, specifically, acetic acid, acrylic acid, methacrylic acid and the like. The molar ratio of the alcohols to the acids is not particularly limited and generally set to 0.1 to 100. For the carboxylic acids, anhydrides may be used. When an ester is produced from an olefin and a fatty acid, the carboxylic acids described above can be used as the fatty acid. The olefins are also not particularly limited, and any one of straight, branched and cyclic ones may be used as well as described above, and olefins having a carbon number of 2 to 5, specifically, propylene, 1-butene, 2-butene and isobutene and the like are preferably used.

The substrate used for the hydrolysis reaction in the invention is not particularly limited as long as the substrate is the compound having an ester bond or ether bond in the molecule. Examples of the compound having an ester bond in the molecule include carboxylic acid ester, phosphoric acid ester, sulfuric acid ester, and the like. Further detailed examples of carboxylic acid esters include fatty acid esters, fatty acid glycerin esters and the like, and also alkyl esters, glycerin esters and the like of saturated or unsaturated fatty acids having a carbon number of 1 to 30, for example, formic acid, acetic acid, propionic acid, butyric acid, valeric acid, lauric acid, palmitic acid, stearic acid, oleic acid, erucic acid, linoleic acid, linolenic acid and the like. With respect to the glycerin ester, any one of monoglyceride, diglyceride, and triglyceride may be used. Examples of the compound having an ether bond in the molecule include, in addition to dialkyl ethers and cyclic ethers, polysaccharides having $\alpha$- or $\beta$-glycoside bond, specifically, maltose, cellobiose, starch, cellulose, and the like.

The ratio of the water to be used in the hydrolysis to the substrate is not particularly limited and generally set to 0.1 to 100 as the molar ratio to the equivalent of the ester bond or ether bond contained in the substrate.

The reaction conditions in the hydration reaction and etherification reaction of olefins can be properly selected. However, when the reaction temperature exceeds 250° C., a catalyst comprising the sulfonic acid group-containing carbonaceous material may decompose during the reaction. When the esterification reaction of carboxylic acids is performed with alcohols and also when the hydrolysis reaction of the compound having an ester bond or ether bond in the molecule is performed, the reaction conditions can be properly selected. In addition, in each of the above-mentioned reactions using a solid acid catalyst comprising the sulfonic acid group-containing carbonaceous material of the invention, the means of reactive distillation can be used.

The reaction pressure is not particularly limited and can be properly selected. When the reaction pressure exceeds 20 MPa, the problem such as an increase in the facility cost is caused.

As the reaction phase, any one of gas phase, liquid phase and gas-liquid mixed phase can be adopted. In the case of the esterification reaction of alcohol with fatty acid, the reaction easily progresses by appropriately removing water generated in accordance with the progress of the reaction from the reaction system.

Upon performing the hydration reaction, a solvent can be used. As the solvent, an amphipathic solvent is preferred so that the reaction solution may not separate into an aqueous phase and an oil phase. For example, ethers, glycol ethers, alcohols, ketones and the like can be used. Although the solvent is usable similarly in the etherification reaction, the solvent is not required unless phase separation occurs.

The hydration reaction of olefins in the invention is a direct hydration method (single stage reaction), and therefore, the process is simpler as compared with an indirect hydration method using a sulfuric acid catalyst (two-stage reaction of sulfuric acid esterification and hydrolysis). Further, the indirect hydration method requires a neutralization and purification step for removal of sulfuric acid, a concentration step for reuse of sulfuric acid, and the like, which complicate the process. However, in the method of the invention, the catalyst can be easily separated by filtration, centrifugal separation or the like for reuse since the catalyst is solid, and the neutralization and purification step as in the indirect hydration method is not required since the reaction solution after removing the catalyst contains no acid catalyst component. After the catalyst removal, reaction product can be appropriately purified by distillation or the like. Reactive distillation can be also applied. In the etherification reaction of olefins in the invention, reactive distillation or a method by fixed bed is generally adopted.

The type of reactor to perform the hydration reaction and etherification reaction of olefins, the esterification reaction of alcohol with carboxylic acid, the esterification reaction of olefin with carboxylic acid, or the hydrolysis reaction of organic compound containing an ester bond or ether bond in the invention is not particularly limited, and any one of batch, continuous and semicontinuous types may be used. Also, any form of reactor, such as tank reactor, column reactor and loop reactor, may be used. The form of contacting the catalyst with the reactant may be any one of suspension phase, fixed bed and the like. In particular, the form that suspends the catalyst in a tank reactor equipped with a stirring apparatus or the form that continuously let a reactant flow through the catalyst as a fixed bed is preferably adopted.

In any case of the hydration reaction and etherification reaction of olefins, the esterification reaction of alcohol with carboxylic acid, the esterification reaction of olefin with carboxylic acid, and the hydrolysis reaction of organic compound containing an ester bond or ether bond, the sulfonic acid group-containing carbonaceous material of the invention is used as a catalyst, whereby the reaction can be driven under high temperature by the excellent heat resistance of the material. As a result, the reaction rate is increased, and miniaturization of a reactor can be attained. Also, due to heat resistance of the catalyst, the frequency of catalyst exchange is decreased.

Hereinafter, the acidolysis reaction of an aralkyl hydroperoxide will be described. The aralkyl hydroperoxide used in the invention is the one whose secondary or tertiary carbon atom in the side chain of an alkyl-substituted aromatic hydrocarbon compound is substituted by hydroperoxide group and has a structure represented by the following chemical formula 1. This substance is decomposed in the presence of an acid catalyst to produce a corresponding phenol and a ketone or aldehyde. Cumene hydroperoxide produces phenol and acetone as represented by the following chemical formula 2.

[Chemical Formula 1]

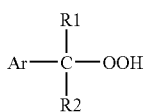

wherein, each of R1 and R2 is an alkyl group or hydrogen atom, and the total carbon atom number of R1 and R2 is 1 or more.

[Chemical Formula 2]

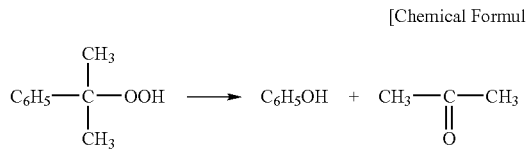

With respect to a method for performing the acidolysis reaction of an aralkyl hydroperoxide, an example of cumene hydroperoxide is described. The reaction is performed in the liquid phase state. As the type of reactor, either a fixed bed flow reactor filled with a solid acid catalyst or batch-wise tank reactor equipped with a stirrer in which a catalyst is suspended in the reaction solution can be used. The reaction temperature is from 50 to 90° C. and preferably from 60 to 80° C. Since the acidolysis reaction of cumene hydroperoxide is an exothermic reaction, if necessary, it is preferred that reaction solution be diluted with an inert diluent in order to slow down the increase in temperature by heat of reaction. When the batch reactor is used, a diluent having a proper boiling point is used, and the diluent is boiled to reflux, whereby it is possible to maintain the reaction temperature and also remove heat of reaction. In the case of batch reaction, the ratio of the sulfonic acid group-containing carbonaceous material of the invention used as a solid acid catalyst is from 1/100 to 1 (weight ratio) of hydroperoxide fed. The reaction time period is preferably from 15 minutes to 8 hours. In the case of fixed bed flow reactor, LHSV of the mixture solution of reaction raw materials is preferably from 0.1 to 1.0 (L-feed/L-catalyst/Hr).

Here, the production of ketone is described. Using a solid acid catalyst comprising the sulfonic acid group-containing carbonaceous material of the invention, a secondary alcohol can be produced by the hydration reaction of an olefin using the above-described method. This secondary alcohol is subjected to dehydrogenation reaction, whereby a corresponding ketone can be produced. For example, 2-propanol obtained by the hydration reaction of propylene is dehydrogenated to give acetone. Also, 2-butanol obtained by the hydration reaction of normal butene is dehydrogenated, whereby methyl ethyl ketone can be produced. The dehydrogenation reaction can be performed by the generally known method. For example, using copper-zinc based catalyst, the reaction can be performed at a reaction temperature of 300 to 500° C. and a pressure of 0 to 1 MPa. Since this dehydrogenation reaction is an endothermic reaction, the higher temperature is more advantageous from the aspect of chemical equilibrium. However, an excessive high temperature is not preferred since the decomposition reaction simultaneously occurs or catalyst sintering occurs, and the temperature range described above is preferred. Also, due to a dehydrogenation reaction, the lower the pressure is, the more advantageously the reaction progresses.

The alcohol produced using the solid acid catalyst comprising the sulfonic acid group-containing carbonaceous material of the invention is inexpensive as compared with an alcohol produced by a method using the conventional sulfuric acid or a method using a heteropoly acid using supercritical conditions, since the production method of the alcohol is easy, does not cause apparatus corrosion and generates few waste. A ketone can be also inexpensively produced by dehydrogenating the alcohol. Namely, the invention can provide an inexpensive, environmentally friendly and economically advantageous method for producing methyl ethyl ketone from normal butene.

The present invention will be specifically described by Examples hereinbelow, and the invention is not limited to these examples. Comparative Example 1 corresponds to Patent Documents 2 and 3, Comparative Examples 2, 6 to 7, and 9 correspond to Patent Document 2, Comparative Examples 3, 4 and 8 correspond to Patent Document 2 and Non-Patent Document 5, Comparative Example 5 corresponds to Patent Document 4 and Non-Patent Document 6, and Comparative Example 10 is a publicly known solid acid catalyst.

(Analysis Method of Sulfonic Acid Group-Containing Carbonaceous Material)

The following analyses were carried out for each of the sulfonic acid group-containing carbonaceous materials obtained in Examples and Comparative Examples.

1. Powder X-Ray Diffraction Analysis

An X-ray diffractometer manufactured by MAC Science Co., Ltd (MXP18VAHF) was used for the analysis.

2. Determination of Acid Group Content

The acid group content was determined by back titration.

3. Elemental Analysis

Elementar Vario EL was used for the analysis. The result was expressed as the ratio of sulfur atom to carbon atom (S/C ratio). This value serves as a measure of the content of the sulfonic acid groups added and introduced into the sulfonic acid group-containing carbonaceous material.

4. Degree of Graphitization

Raman spectroscopy was performed for the purpose of examining the degree of graphitization. A laser Raman spectroscopic analyzer HOLOLAB5000R was used for the analysis. The peak intensity ratio of D-peak which appears near 1400 $cm^{-1}$ to G-peak which appears near 1580 $cm^{-1}$ in Raman spectroscopy is generally used as measure of the degree of graphitization. However, while the reason is unknown, the sulfonic acid group-containing carbonaceous materials of the invention did not give a clear spectrum as shown in Examples, so that the degree of carbonization could not be calculated. On the other hand, for a sulfonated carbonaceous material in each of Comparative Examples, D-peak and G-peak were clearly found.

5. Proton Conductivity

The proton conductivities of the sulfonic acid group-containing carbonaceous materials of Examples 6 and 7 and Comparative Examples 8 and 9 were determined using AC impedance method. At a temperature of 50° C. and a relative humidity of 100%, the measurement was made according to the following procedures.

(Pretreatment of Sample)

The amount 0.1 g of powder sample is formed into tablet with a diameter of 14 mm and a thickness of from 50 to 800 μm using a tablet forming machine (pressure of 550 kgf/cm$^2$, retention time of 5 minutes). The resulting sample is put in a glass container, further put in a container with plug to which distilled water is added, and retained in a thermostat bath at 50° C. for 12 hours or more.

(Determination of Proton Conductivity)

A small container (with distilled water, lid opened) is put in a jacketed glass cell, and the temperature inside the cell is maintained at 50° C. for 12 hours or more. The pretreated sample is sandwiched between two platinum plates (thickness of 0.05 mm), and the top and bottom of the platinum plates are further sandwiched between stainless plates (thickness of from 1 to 1.5 mm). This is fixed to an exclusive tool, connected to a lead, and then put in the jacketed glass cell and allowed to stand for 1 hour. AC voltage is applied to perform an impedance measurement, and the proton conductivity is calculated from the resulting impedance. The result is shown in Table 1 and Table 2.

EXAMPLES

Example 1

Production of Sulfonic Acid Group-Containing Carbonaceous Material

Forty grams of powder of a composition (PHENOLITE (registered trademark) manufactured by DIC Corporation, TD-739A) which was prepared by compounding an 8% by mass of a curing agent, hexamethylenetetramine, to a novolac type phenolic resin was put in a egg plant-shaped flask with a capacity of 1000 ml and heat-treated at 400° C. for 4 hrs under nitrogen flow to give 8.4 g of carbonized material. To 3.0 g of the resulting black powder carbonized material was added 150 g of fuming sulfuric acid, and the mixture was heat-treated at 150° C. for 7.5 hrs under nitrogen atmosphere to perform sulfonation. After the sulfonation, a black solid matter was filtered with a glass filter, and the filtration residue was repeatedly washed with hot water under reflux (about 100° C.) using a Soxhlet extractor to confirm that no sulfuric acid was detected in the washing water. The resulting substance was dried to give a black powder sulfonic acid group-containing carbonaceous material A. Each analysis described above was carried out with the resulting sulfonic acid group-containing carbonaceous material.

Powder X-ray Diffraction Analysis: No peak that could specify the structure was detected from the diffraction pattern, so that the sulfonic acid group-containing carbonaceous material A was found to be substantially amorphous. The sulfonic acid group-containing carbonaceous materials B to J obtained in other Examples and Comparative Examples were also substantially amorphous.

Determination of Acid Group Content: The result is shown in Table 1. The results of the sulfonic acid group-containing carbonaceous materials obtained in other Examples and Comparative Examples are also shown in Table 1 or Table 2.

Elemental Analysis (S/C Ratio): The result is shown in Table 1. The results of the sulfonic acid group-containing carbonaceous materials obtained in other Examples and Comparative Examples are also shown in Table 1 or Table 2.

Degree of Graphitization (Raman Spectroscopy): The sulfonic acid group-containing carbonaceous material A did not give a clear spectrum, so that the degree of carbonization could not be obtained from the intensity ratio of G-peak and D-peak. In addition, the sulfonic acid group-containing carbonaceous materials obtained in the other Examples could not also give a clear spectrum. On the other hand, the sulfonic acid group-containing carbonaceous materials obtained in Comparative Examples gave a clear spectrum, so that the degree of carbonization could be obtained.

(Hydration Reaction of Propylene)

An autoclave reactor with an inner volume of 200 ml and equipped with a stirrer was charged with 9.0 g of distilled water (0.5 mol) and 15.0 g of dioxane (solvent), 0.20 g of the sulfonic acid group-containing carbonaceous material A was added thereto, and the reactor was hermetically closed and substituted with nitrogen. Thereafter, 10.5 g of propylene (0.25 mol) was injected thereto and sealed therein. Subsequently, the mixture was heated to 120° C. while stirring at 700 rpm, and the pressure was adjusted to 5.0 MPa with nitrogen. Thereafter, the hydration reaction was performed for 2 hrs while the temperature was maintained at 120° C. After completion of the reaction, the reaction solution was cooled, and the quantitative analysis of the product was performed by a gas chromatograph with TCD detector. As a result, the amount of isopropyl alcohol produced, calculated per unit catalyst amount and unit time, was 1.46 mmol/g-cat./hr. The result is shown in Table 1. (Example 2 and Comparative Examples 1 to 5)

(Production of Sulfonic Acid Group-Containing Carbonaceous Materials)

Using the same procedures as in Example 1 described above except using the raw materials and the conditions of carbonization and sulfonation described in Table 1, sulfonic acid group-containing carbonaceous materials B to G were each produced. All the novolac resins used as the raw material are the same one as used in Example 1. Also, as heavy oil A, the one collected in Nippon Oil Corporation refinery for test was used, and as naphthalene and D-glucose, the commercially available powder reagents were directly used.

(Hydration Reaction of Propylene)

Using the same conditions and procedures as in Example 1 described above except using the sulfonic acid group-containing carbonaceous materials B to G obtained in Example 2 and Comparative Examples 1 to 5 described above in place of the sulfonic acid group-containing carbonaceous material A as a catalyst, the hydration reactions of propylene were each performed. The amounts of isopropyl alcohol produced, calculated per unit catalyst amount and unit time, are shown in Table 1.

Example 3

Hydration Reaction of Butene-1

The same reaction apparatus as the one used in the hydration reaction of propylene was charged with 9.0 g of distilled water (0.5 mol) and 15.0 g of dioxane (solvent), 0.20 g of the sulfonic acid group-containing carbonaceous material B obtained in Example 2 described above was added thereto, and the reaction apparatus was hermetically closed. Then, 14.3 g of butene-1 (0.25 mol) was injected thereto and sealed therein. Subsequently, the mixture was heated to 150° C. while stirring at 700 rpm, and the pressure was adjusted to 5.0 MPa with nitrogen. Thereafter, the hydration reaction was performed for 2 hours while the temperature was maintained at 150° C. After completion of the reaction, the reaction solution was cooled, and the quantitative analysis of the product was performed using a gas chromatograph with TCD detector. As a result, the amount of 2-butanol produced, calculated per unit catalyst amount and unit time, was 3.44 mmol/g-cat./hr.

Comparative Example 6

Hydration Reaction of Butene-1

Using the same conditions and procedures as in Example 3 described above except using the sulfonated carbonaceous material E obtained in Comparative Example 3 described above in place of the sulfonic acid group-containing carbonaceous material B as a catalyst, the hydration reaction of butene-1 was performed. As a result, the amount of 2-butanol produced, calculated per unit catalyst amount and unit time, was 1.52 mmol/g-cat./hr.

Example 4

Diisopropyl Ether Synthesis

The same reaction apparatus as the one used in the hydration reaction of propylene was charged with 15 g of isopropyl alcohol (0.25 mol), 0.20 g of the sulfonic acid group-containing carbonaceous material B was added thereto as a catalyst, and the reaction apparatus was hermetically closed and substituted with nitrogen. Thereafter, 21 g of propylene (0.5 mol) was injected thereto and sealed therein. Subsequently, the mixture was heated to 110° C. while stirring at 700 rpm, and the pressure was adjusted to 5.0 MPa with nitrogen. Thereafter, the etherification reaction was performed for 2 hours while the temperature was maintained at 110° C. After completion of the reaction, the reaction solution was cooled, and the quantitative analysis of the product was performed by a gas chromatograph with TCD detector. As a result, the amount of diisopropyl ether produced, calculated per unit catalyst amount and unit time, was 3.03 mmol/g-cat./hr.

Comparative Example 7

Diisopropyl Ether Synthesis

Using the same conditions and procedures as in Example 4 described above except using the sulfonic acid group-containing carbonaceous material E in place of the sulfonic acid group-containing carbonaceous material B as a catalyst, the synthesis reaction of diisopropyl ether was performed. As a result, the amount of diisopropyl ether produced, calculated per unit catalyst amount and unit time, was 1.60 mmol/g-cat./hr.

Example 5

Synthetic Reaction of Ethyl Acetate

A egg plant-shaped flask with an inner volume of 50 ml was charged with 7.7 ml of ethanol, acetic acid was added thereto so as to have a molar ratio to alcohol of 1/10, 0.20 g of the sulfonic acid group-containing carbonaceous material B was added thereto, and the mixture was heated. The mixture was reacted for 1 hour at reflux temperature (80° C.) while stirring and thereafter rapidly cooled in a water bath to terminate the reaction. After completion of the reaction, the yield of ethyl acetate was calculated by a gas chromatograph with FID detector. As a result, the yield of ethyl acetate was 57% (mol of ethyl acetate/mol of fed acetic acid).

Example 6

Hydrolysis of Ethyl Acetate

A egg plant-shaped flask with an inner volume of 100 ml was charged with 2.6 g of ethyl acetate (0.030 mol), 27 g of water (50 times of ethyl acetate in molar ratio) was added thereto, 0.20 g of the sulfonic acid group-containing carbonaceous material A obtained in Example 1 described above was further added thereto, and the mixture was heated. The mixture was reacted for 2 hours at reflux temperature (80° C.) while stirring and thereafter rapidly cooled in a ice bath to terminate the reaction. After completion of the reaction, the quantitative analysis of the product was performed using a gas chromatograph with TCD detector. As a result, the rate of conversion of ethyl acetate to acetic acid was 64% (mol of produced acetic acid/mol of fed ethyl acetate).

Comparative Example 8

Hydrolysis of Ethyl Acetate

Using the same conditions and procedures as in Example 6 described above except using the sulfonic acid group-containing carbonaceous material F in place of the sulfonic acid group-containing carbonaceous material A as a catalyst, the hydrolysis reaction of ethyl acetate was performed. As a result, the rate of conversion of ethyl acetate to acetic acid was 36% (mol of produced acetic acid/mol of fed ethyl acetate).

Example 7

Production of Sulfonic Acid Group-Containing Carbonaceous Material

Using the same raw materials, conditions and procedures as in Example 1 described above except that the carbonization conditions are changed to 350° C. and 30 hrs, sulfonic acid group-containing carbonaceous material H was obtained. Properties and proton conductivity value of the sulfonic acid group-containing carbonaceous material H are shown in Table 2.

Example 8 and Comparative Example 9

Production of Sulfonic Acid Group-Containing Carbonaceous Materials

Using the same procedures as in Example 7 described above except using raw materials, carbonization conditions and sulfonation conditions shown in Table 2, sulfonic acid group-containing carbonaceous material I (Example 8) and sulfonic acid group-containing carbonaceous material J (Comparative Example 9) were each produced. Properties and proton conductivity values of these materials are shown in Table 2.

Comparative Example 10

Determination of Proton Conductivity of NAFION

The proton conductivity of super strong acid fluorine-containing polymer manufactured by DuPont, NAFION (registered trademark) 112 (membrane with a thickness of 0.002 inches) was determined. The result is shown in Table 2.

Example 9

Acidolysis Reaction of Cumene Hydroperoxide

The acidolysis reaction was performed by decomposing cumene hydroperoxide to produce phenol. A 100-cc three-necked flask was charged with 13.8 g of ethanol and 0.2 g of a solid acid catalyst comprising the sulfonic acid group-containing carbonaceous material A, and the mixture was heated to 78° C. and stirred under nitrogen atmosphere (ethanol was in reflux condition). Thereto was added dropwise 15.2 g of cumene hydroperoxide (content of 88% by mass). In two hours after completion of the dropwise addition, the reaction solution was cooled, and the quantitative analysis was performed by LC. As a result, the yield of phenol was 45% (mol of phenol/mol of fed cumene hydroperoxide).

Example 10

Synthetic Reaction of Methyl Ethyl Ketone

A 500-cc autoclave equipped with a stirrer was charged with 45.0 g of distilled water (2.5 mol), 4.0 g of a solid acid catalyst comprising the sulfonic acid group-containing carbonaceous material A was added thereto, and the autoclave was hermetically closed. Then, 92.5 g of butene (1.25 mol) was injected thereto and sealed therein. Subsequently, the mixture was heated to 150° C. while stirring at 700 rpm, and the pressure was adjusted to 5 MPa with nitrogen. Thereafter, the hydration reaction was performed for 7.5 hours while the temperature was maintained at 150° C. After completion of the reaction, the reaction solution was cooled, and the quantitative analysis was performed by a TCD-GC to confirm that 7.6 g of 2-butanol was obtained. The reaction solution was thereafter distilled and further dehydrated with molecular sieve to give 7.2 g of 2-butanol with a purity of 90%.

A 100-cc autoclave equipped with a stirrer was charged with 1.0 g of 2-butanol obtained and 0.1 g of copper-zinc catalyst (manufactured by Sigma-Aldrich Corporation) and hermetically closed. Subsequently, the mixture was heated to 500° C. while stirring at 700 rpm, and the dehydrogenation reaction was performed for 1 hour. After completion of the reaction, the reaction solution was cooled, and the quantitative analysis was performed by a TCD-GC, to confirm that 0.58 g of methyl ethyl ketone was obtained.

Example 11

Production of Sulfonic Acid Group-Containing Carbonaceous Material

A sulfonic acid group-containing carbonaceous material was produced using a resol type phenolic resin. A resol type phenolic resin used was Super Beckacite (registered trademark) TD-773 manufactured by DIC Corporation. The same production conditions as used in the sulfonic acid group-containing carbonaceous material B described in Example 2 was used to give sulfonic acid group-containing carbonaceous material K. The yield of carbonized material was 50%, the acid content was 2.98 mmol/g, and the sulfur/carbon ratio was $1.7 \times 10^{-2}$.

(Synthetic Reaction of Ethyl Acetate)

Using the same conditions as in Example 5 except using the sulfonic acid group-containing carbonaceous material K in place of the sulfonic acid group-containing carbonaceous material B as a catalyst, the synthetic reaction of ethyl acetate was performed. As a result, the yield of ethyl acetate was 56% (mol of ethyl acetate/mol of fed acetic acid).

Comparative Example 11

Using the same conditions as in Example 11 except using the sulfonic acid group-containing carbonaceous material E in place of the sulfonic acid group-containing carbonaceous material K as a catalyst, the synthetic reaction of ethyl acetate was performed. As a result, the yield of ethyl acetate was 43% (mol of ethyl acetate/mol of fed acetic acid), which was lower than that in the case of using the sulfonic acid group-containing carbonaceous material K produced using a resol type phenolic resin.

Example 12

Acetate Ester Synthesis from Olefin and Acetic Acid

The esterification reaction of an olefin was performed using the sulfonic acid group-containing carbonaceous material B. A 100-cc autoclave equipped with a stirrer was charged with 30.3 g of acetic acid (0.50 mol), 0.5 g of the sulfonic acid group-containing carbonaceous material B was added thereto, and the autoclave was hermetically closed. Then, 13.0 g of propylene (0.31 mol) was injected thereto and sealed therein. Subsequently, the mixture was heated to 130° C. while stirring at 200 rpm, and the pressure was adjusted to 2.5 MPa with nitrogen. Thereafter, the esterification reaction was performed for 90 minutes. After completion of the reaction, the reaction solution was cooled, and the quantitative analysis was performed by a FID-GC to confirm that 3.2 g of isopropyl acetate was obtained.

It has been shown from the above results that, the sulfonic acid group-containing carbonaceous materials of the present invention have a structural difference, as compared with the sulfonic acid group-containing carbonaceous material according to the conventional art, in that a clear spectrum is not obtained in Raman spectroscopy, and it proves that the materials of the invention have high activities, as a solid acid catalyst, for the hydration reaction and etherification reaction of olefins, the esterification reaction of an alcohol with a carboxylic acid, or the esterification reaction of an olefin with a carboxylic acid, the hydrolysis reaction of an organic compound comprising an ester bond or ether bond, and have excellent proton conductivity as a proton conductor material. In addition, it has been found that the sulfonic acid group-containing carbonaceous materials of the invention were highly effective as a catalyst for decomposing hydroperoxide such as cumene hydroperoxide.

In addition, it has been shown that a secondary alcohol obtained by the hydration reaction of an olefin using a solid acid catalyst comprising the sulfonic acid group-containing carbonaceous material of the invention is dehydrogenated, whereby ketones, particularly methyl ethyl ketone, can be economically advantageously produced.

INDUSTRIAL APPLICABILITY

As described above, according to the present invention, the sulfonic acid group-containing carbonaceous material having activities as a solid acid catalyst for reactions such as the hydration of olefins and also having excellent proton conductivity and the method for producing the same can be provided. Therefore, the sulfonated carbonaceous material of the invention is particularly useful as a catalyst for above-described reactions or as a solid electrolyte suitable for use in a battery or the like. In addition, according to the present invention, ketones, particularly methyl ethyl ketone, can be more advantageously produced via a hydration reaction of olefins, as compared with the conventional method.

TABLE 1

| | Production of Sulfonic Acid Group-Containing Carbonaceous Material | | | | | | | | Property of Sulfonic Acid Group-Containing Carbonaceous Material | | | Hydration Reaction of Propylene |
|---|---|---|---|---|---|---|---|---|---|---|---|---|
| | Sulfonic Acid Group-Containing Carbonaceous | | Carbonization Condition | | Sulfonation Condition | | | Yield of Carbonized | Acid Group | Sulfur/ Carbon | Raman Spectrum | Amount of Isopropyl Alcohol |
| Example | Material | Raw Material | Temperature (°C.) | Time (hr) | Sulfonating Agent | Temperature (°C.) | Time (hr) | material (%) | Content (mmol/g) | Ratio (×10⁻²) | D/G Peak Intensity Ratio | Produced (mmol/ g-cat./hr) |
| Example 1 | A | Novolac Resin/ Hexamine | 400 | 4 | Fuming Sulfuric Acid | 150 | 7.5 | 21 | 3.85 | 6.0 | No Peak Obtained | 1.46 |
| Example 2 | B | Novolac Resin/ Hexamine | 500 | 4 | Fuming Sulfuric Acid | 150 | 7.5 | 18 | 2.84 | 3.4 | No Peak Obtained | 0.78 |
| Comparative Example 1 | C | Heavy Oil A | Carbonization and Sulfonation Simultaneously Performed | | Fuming Sulfuric Acid | 100 | 1 | — | 3.41 | — | 0.57 | 0.57 |
| Comparative Example 2 | D | Naphthalene | Carbonization and Sulfonation Simultaneously Performed | | Concentrated Sulfuric Acid | 250 | 15 | — | 2.70 | — | 0.59 | 0.60 |
| Comparative Example 3 | E | D-Glucose | 400 | 5 | Concentrated Sulfuric Acid | 150 | 15 | 29 | 3.05 | 1.7 | 0.57 | 0.34 |
| Comparative Example 4 | F | D-Glucose | 400 | 15 | Fuming Sulfuric Acid | 150 | 15 | 26 | 3.10 | — | 0.59 | 0.30 |
| Comparative Example 5 | G | Novolac Resin/ Hexamine | 800 | 1 | Concentrated Sulfuric Acid | 150 | 7.5 | 14 | 0.37 | 0 | 0.88 | 0 |

TABLE 2

| | Production of Sulfonic Acid Group-Containing Carbonaceous Material | | | | | | | | Property of Sulfonic Acid Group-Containing Carbonaceous Material | | | |
|---|---|---|---|---|---|---|---|---|---|---|---|---|
| | Sulfonic Acid Group-Containing Carbonaceous | | Carbonization Condition | | Sulfonation Condition | | | Yield of Carbonized | Acid Group | Sulfur/ Carbon | Raman Spectrum | Proton |
| Example | Material | Raw Material | Temperature (°C.) | Time (hr) | Sulfonating Agent | Temperature (°C.) | Time (hr) | material (%) | Content (mmol/g) | Ratio (×10⁻²) | D/G Peak Intensity Ratio | Conductivity (10⁻³ S/cm) |
| Example 7 | H | Novolac Resin/ Hexamine | 350 | 30 | Fuming Sulfuric Acid | 150 | 7.5 | 23 | 4.16 | 5.5 | No Peak Obtained | 25.0 |
| Example 8 | I | Novolac Resin/ Hexamine | 350 | 30 | Concentrated Sulfuric Acid | 150 | 7.5 | 23 | 3.84 | 2.5 | No Peak Obtained | 7.6 |
| Comparative Example 9 | J | D-Glucose | 400 | 4 | Concentrated Sulfuric Acid | 150 | 7.5 | 26 | 2.54 | — | 0.57 | 2.1 |
| Comparative Example 10 | | | | | NAFION 112 | | | | 0.89[1] | — | — | 12.0 |

[1] Catalog Value

The invention claimed is:

1. A method for producing a product, comprising effecting a reaction in the presence of a solid acid catalyst comprising a solid sulfonic acid group-containing carbonaceous material that is the product of carbonization and sulfonation of a phenolic resin and is in powdery form at the stage of production, wherein the reaction is selected from the group of (a) hydrating an olefin, (b) etherifying an olefin, (c) esterifying a carboxylic acid, (d) hydrolyzing a reactant selected from the group of an organic compound containing an ester bond or ether bond or both, and (e) acidolysis of an aralkyl hydroperoxide.

2. The method according to claim 1 in which the reaction comprises hydrating an olefin in the presence of the solid acid to produce a hydration product.

3. The method according to claim 1 in which the reaction comprises performing an olefin etherification reaction in the presence of the solid acid catalyst to form an ether.

4. The method according to claim 1 in which the reaction comprises performing esterification by reacting a carboxylic acid with an alcohol in the presence of the solid acid catalyst to produce an ester.

5. The method according to claim 1 in which the reaction comprises reacting a carboxylic acid with an olefin in the presence of the solid acid catalyst to form an ester.

6. The method according to claim 1 in which the reaction comprises hydrolyzing an organic compound containing an ester bond or ether bond or both in the presence of the solid acid catalyst to form an alcohol, a fatty acid, or both.

7. A method for producing a ketone, comprising dehydrogenating the olefin hydration product obtained in claim 2.

8. The method for producing a ketone according to claim 7, characterized in that the olefin hydration product is 2-butanol, and a ketone obtained by the dehydrogenation reaction is methyl ethyl ketone.

9. The method according to claim 1 in which the reaction comprises acidolysis of an aralkyl hydroperoxide in the presence of the solid acid catalyst to form a phenol.

10. The method according to claim 9, characterized in that the aralkyl hydroperoxide is cumene hydroperoxide, and the phenol produced is phenol.

* * * * *

UNITED STATES PATENT AND TRADEMARK OFFICE
CERTIFICATE OF CORRECTION

```
PATENT NO.       : 8,575,281 B2                                    Page 1 of 1
APPLICATION NO.  : 12/528051
DATED            : November 5, 2013
INVENTOR(S)      : Yanagawa et al.
```

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 852 days.

Signed and Sealed this
Twenty-second Day of September, 2015

Michelle K. Lee
*Director of the United States Patent and Trademark Office*